United States Patent
Peña

(10) Patent No.: US 7,629,007 B2
(45) Date of Patent: Dec. 8, 2009

(54) PROCESS FOR PURIFICATION OF FREE XANTHOPHYLLS

(75) Inventor: Gustavo Rodriguez Peña, Sinaloa (MX)

(73) Assignee: Industrias Vepinsa, S.A. de C.V., Los Mochis, Sinaloa (MX)

( * ) Notice: Subject to any disclaimer, the term of this patent is extended or adjusted under 35 U.S.C. 154(b) by 311 days.

(21) Appl. No.: 11/640,570

(22) Filed: Dec. 18, 2006

(65) Prior Publication Data

US 2007/0161826 A1    Jul. 12, 2007

Related U.S. Application Data

(60) Provisional application No. 60/751,672, filed on Dec. 19, 2005.

(51) Int. Cl.
*A61K 36/00*    (2006.01)

(52) U.S. Cl. ...................................... 424/725; 424/777

(58) Field of Classification Search ........................ None
See application file for complete search history.

(56) References Cited

U.S. PATENT DOCUMENTS

| 3,333,962 | A  | * | 8/1967  | Prebluda et al. ............. 424/764 |
| 6,329,557 | B1 |   | 12/2001 | Rodriguez et al. |
| 6,504,067 | B1 |   | 1/2003  | Montoya-Olvera et al. |
| 7,109,361 | B2 | * | 9/2006  | Hoffman et al. ................ 554/8 |
| 7,138,152 | B2 | * | 11/2006 | Allen et al. .................. 426/429 |
| 7,150,890 | B2 | * | 12/2006 | Rosales et al. .............. 424/778 |
| 2004/0176475 | A1 |   | 9/2004  | Hoffman et al. |
| 2005/0153002 | A1 | * | 7/2005  | Socla Rosales et al. ..... 424/764 |
| 2007/0032683 | A1 | * | 2/2007  | Xu et al. ..................... 568/816 |

OTHER PUBLICATIONS

International Search Report dated Jan. 23, 2008.

* cited by examiner

*Primary Examiner*—Christopher R. Tate
(74) *Attorney, Agent, or Firm*—Knobbe, Martens, Olson & Bear LLP

(57) ABSTRACT

A simple and economic method of extracting free xanthophylls from plant material, particularly marigold petals and boxthorn berries, is described. The method relies upon salting out of aqueous components from a saponified oleoresin, which limits the use of organic solvents during the extraction and is also very economical.

20 Claims, 2 Drawing Sheets

PROCESS FOR PURIFICATION OF FREE XANTHOPHYLLS

RELATED APPLICATIONS

This application claims priority to U.S. Provisional Application No. 60/751,672, filed Dec. 19, 2005 which is incorporated herein by reference.

BACKGROUND OF THE INVENTION

1. Field of the Invention

The present invention relates to a process for purification of xanthophylls from plant extracts, particularly marigold oleoresins.

2. Description of the Related Art

The carotenoids comprise a group of natural pigments found abundantly in plants, some fish, crustaceans, birds, algae and bacteria. Within this group of pigments are the yellow carotenoids, including both the carotenes (e.g., β-carotene) and xanthophylls (e.g., lutein and zeaxanthin), and the red carotenoids, including capsanthin, canthaxanthin and astaxanthin. These yellow and red carotenoids are often present in plants, especially flowering plants, together with other classes of pigments, including primarily green chlorophyll pigments.

Carotenoids and in particular, xanthophylls, from marigold extracts have been used for decades in the poultry industry for pigmentation of broiler skins and egg yolks. Lutein, is present at much higher concentrations than zeaxanthin in marigold extracts. Pigmenting formulations for use in the poultry industry having relatively high concentrations of zeaxanthin are known, wherein the lutein has been isomerized to yield zeaxanthin (U.S. Pat. No. 5,523,494 to Torres and U.S. Pat. No. 5,973,211 to Rodriguez).

In addition to their commercial importance in the poultry industry, the carotenoids have recently received considerable attention from scientists with respect to their potential role in promoting human health. Compounds like α and β-carotene, lutein and zeaxanthin have been shown to possess strong antioxidant activity, which may retard or prevent diseases like cancer, arteriosclerosis, cataracts, macular degeneration and others (Bowen, WO98/45241). Lutein and zeaxanthin are the only carotenoids present in the macular region of the human retina and are related to the normal function of the macula responsible for visual acuity. It has also been reported that carotenoids enhance the immune response. Free radicals produced as byproducts of metabolic processes and originating from environmental pollutants (such as nitrogen dioxide and ozone of polluted air, heavy metals, halogenated hydrocarbons, ionizing radiation and cigarette smoke) are implicated as causative factors in many of the above-mentioned diseases. Carotenoids are potent quenchers of the highly reactive oxygen free radicals that can initiate a cascade of detrimental chemical reactions. Carotenoids also function as chain-breaking antioxidants, especially at low partial pressures of oxygen. Thus, carotenoids can work to quench free radical-induced reactions and can also prevent generation of free radicals, thereby limiting free radical/oxidative damage.

Khachik has described (U.S. Pat. No. 5,382,714) a process for obtaining lutein, the purity of which is usually greater than 90%, determined by UV/visible spectro-photometry. The purity of the lutein was found to be around 94.79%, its isomers around 3.03% based on HPLC analysis and others consisting of zeaxanthin, etc. The main drawback of the above mentioned process is in the use of a halogenated solvent. Halogenated solvents are banned for use in human food applications in most of the countries because of apprehensions about their potential carcinogenic effects.

Ausich and Sanders (U.S. Pat. No. 5,648,564) have developed a process for obtaining xanthophyll crystals containing approximately 70-85% total carotenoids, deemed to contain substantially pure xanthophylls. The HPLC analysis of the xanthophylls showed 85-95% trans-lutein, 0.2-1.5% of its geometrical isomers, 2.5-8% zeaxanthin. The poor solubility of xanthophyll esters in propylene glycol and the subsequent heating to temperatures around 70° C. for 10 hours are the main disadvantages of the above mentioned process, since the lutein undergoes isomerization and decomposition under the above conditions. Further, propylene glycol is not a cost-affordable solvent from commercial considerations.

Khachik in his U.S. Pat. No. 6,262,284 has developed a process for obtaining lutein and zeaxanthin crystals (97% pure) starting from marigold meal instead of marigold extract. This process involved simultaneous extraction and saponification of xanthophyll esters. The main limitations in the above process are saponification of the extract without concentration leading to consumption of large volumes of solvents that are difficult to manage in commercial production. Further formation of peroxides from solvents like THF may cause degradation of the xanthophylls. Also, the use of silica-gel column chromatography is a cumbersome and less economic process for commercial scale production of pure lutein crystals.

Madhavi and Kagan (U.S. Pat. No. 6,380,442) have reported a process for the isolation of mixed carotenoids from plants and illustrated the same with examples of marigold oleoresin. The hydrolysis temperature is high and the reaction time is long leading to lutein oxidation and degradation. The method is not attractive for commercial applications since the water required is more than 30 times per kg of the input material and the lutein is released as minute crystals dispersed in a slimy soapy solution making recovery difficult.

Rodriguez et al. (U.S. Pat. No. 6,329,557) have disclosed an industrial scale process for obtaining xanthophyll crystals from marigold extract. The method is useful for marigold oleoresins and provides an industrial scale process for obtaining lutein and zeaxanthin concentrates of high purity using saponified marigold extracts.

Montoya, et al (U.S. Pat. No. 6,504,067) describe a process for cleaning oleoresin with alkali and acid. The cleaned oleoresin is subjected to aqueous alkali hydrolysis at a temperature of 90° C. for 8 hours in the presence of emulsifiers. This method suffers the disadvantage that high temperature and long cycle time leads to degradation of free lutein.

Kumar, et al. (U.S. Pat. No. 6,743,953) disclose a method which includes saponification in an alcohol to avoid addition of water, removing the alcohol under reduced pressure, and extraction of xanthophylls in ethyl acetate to obtain xanthophylls in good yield. The method of Kumar, et al. avoids the use of water during saponification so that steps to remove the water using organic solvents, particularly halogenated organic solvents, can be avoided. Saponification in alcohol was known as taught by Grant (U.S. Pat. No. 3,523,138).

Sadano, et al. (U.S. 2004/0055954) discloses extraction of marigold oleoresin with supercritical fluid extraction such as high pressure carbon dioxide. Selective extraction is achieved by changing the pressure of the supercritical fluid. The extracted oleoresin is further purified by dissolving in a ketone solvent and removing the precipitate. The requirement for special equipment for supercritical fluid extraction makes this method unattractive for commercial applications.

Khachik (U.S. Application No. 2005/0038271) disclose a method of extracting zeaxanthin from *Lycium Chinese* Mill berries and lutein from marigold without using harmful organic solvents. The method employs tetrahydrofuran and an FDA Class 3 alcohol, preferably ethanol, as the extraction solvents. However, as mentioned above, formation of peroxides from solvents like THF may cause degradation of the xanthophylls.

Quesnel (U.S. Application No. 2005/0139145) discloses a relatively simple method of purifying carotenoids which include lutein using organic solvents. The crystals obtained by this procedure were high in all trans lutein.

Rosales, et al. (U.S. Application No. 2005/0153002) disclose a process to obtain xanthophylls in good yield and high purity that are free from epoxized derivatives. The method includes drying marigold flowers under mild conditions to avoid formation of epoxides, followed by saponification and use of metallic halogenides (e.g. calcium chloride) to remover fatty acids. The resulting precipitate is removed and washed with polar solvent (eg. Alcohol, acetone).

Bhaskaran, et al. (U.S. Application No. 2005/0182280) disclose a method of preparing a stable lutein paste from oleoresin using relatively low temperatures and short reaction times. However, the method includes multiple steps such as dissolving in alcohol, cleaning on an ion exchange resin, hydrolysis of the esters using a phase-transfer catalyst, quenching with an acidic solution, dissolving and filtering the solids, drying the esters, triturating the residue, and distilling the alcoholic fraction. Accordingly, the described method is not a commercially viable method in view of the large number of steps involved.

Clearly there remains a need for a simple, adaptable method for isolation of free xanthophylls that limits the use of organic solvents and minimizes degradation and epoxide levels in the xanthophyll product. Preferred embodiments of the present invention are directed to an improved process for the isolation of xanthophylls, which are free of epoxide derivatives, from plant extracts which is adaptable, economic and easy to carry out.

SUMMARY OF THE INVENTION

Embodiments of the invention are directed to methods for obtaining free xanthophylls which include one or more of the following steps. A plant-derived oleoresin is provided. The plant-derived oleoresin is saponified to obtain a saponified resin. The saponified resin is washed with a salt solution, preferably more than once and preferably until the pH of the resin is about 6.5 to 9. The resin is then washed with a non-polar solvent to remove lipid components. The resin is washed at least once with an increased polarity solvent. The resin is then washed with water to remove solvent. The resin is filtered and/or dried to obtain free xanthophylls.

In preferred embodiments, the plant-derived oleoresin is derived from marigold (*Tagetes erecta*) or boxthorn berries (*Lycium chinensis*).

Preferably, the salt solution comprises a sodium or potassium salt at a concentration of 5 to 15%. More preferably, the salt is a sodium salt and the sodium salt is sodium chloride. Preferably, at least one of the salt solution washes is acidified. More preferably, the last salt solution wash is acidified. In more preferred embodiments, at least one salt solution wash is acidified with 2-3% phosphoric acid.

In preferred embodiments, the increased polarity solvent is a water:alcohol solution or a water:acetone solution. More preferably, the resin is washed with the increased polarity solvent 2-4 times and the polarity of the first wash is less than the polarity of the last wash. Yet more preferably, the increased polarity solvent is acidified for at least one wash. In a preferred embodiment, the resin is washed at least once with an increased polarity solvent which is acidified with 1-3% phosphoric acid. In a most preferred embodiment, the increased polarity solvent includes an acidified water:methanol (10:90) solution for at least one of the washes. In some embodiments, washing the resin with the increased polarity solvent also includes a filtering step.

In some preferred embodiments, the plant is marigold and the free xanthophylls are predominantly free lutein, preferably at least 60% free lutein. In some preferred embodiments the plant is boxthorn berries and the free xanthophylls are predominantly zeaxanthin.

Preferably, the non-polar solvent is hexane.

In preferred embodiments, the final drying step also includes the addition of an alcohol:water mixture to facilitate removal of water. Preferably, the alcohol:water mixture is ethanol:water (50:50).

In some embodiments the oleoresin is provided by one or more of the following steps:

treating a plant homogenate with an increased polarity solvent for an initial purification;

filtering the homogenate to obtain precipitated material; and extracting the precipitated material with a non-polar solvent.

Preferably, the plant is *Lycium chinensis*. Preferably, the increased polarity solvent is a water: alcohol solution. Preferably, the non-polar solvent is hexane.

In some preferred embodiments, the method also includes the steps of concentrating the extract in the non-polar solvent extracts, and/or washing the concentrate with water.

Further aspects, features and advantages of this invention will become apparent from the detailed description of the preferred embodiments which follow.

BRIEF DESCRIPTION OF THE DRAWING

These and other feature of this invention will now be described with reference to the following drawing of preferred embodiments which is intended to illustrate and not to limit the invention.

The FIGURE shows a flow chart for the purification of lutein from saponified marigold extract.

DETAILED DESCRIPTION OF THE PREFERRED EMBODIMENT

Figure 1:
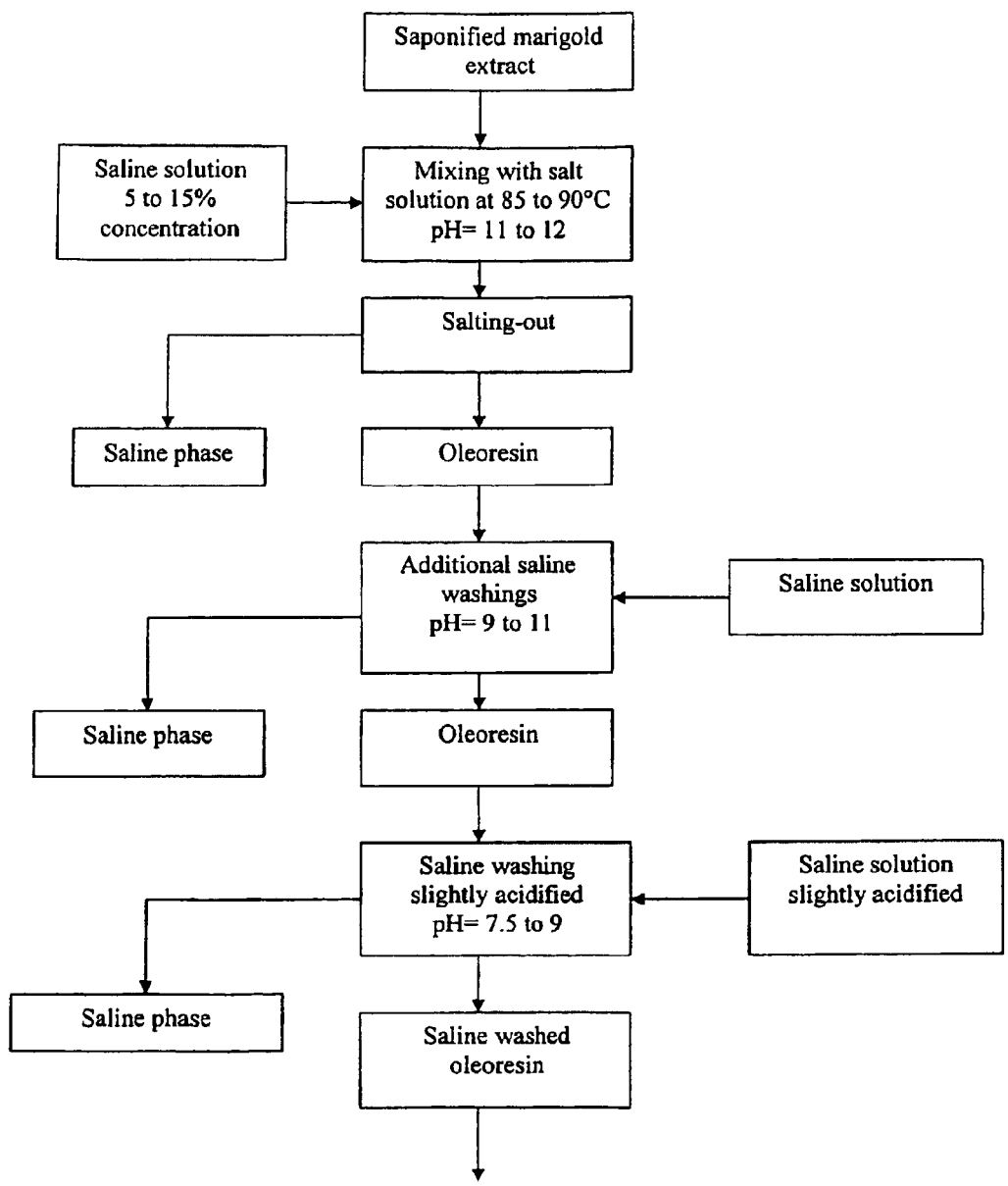
Figure 1:
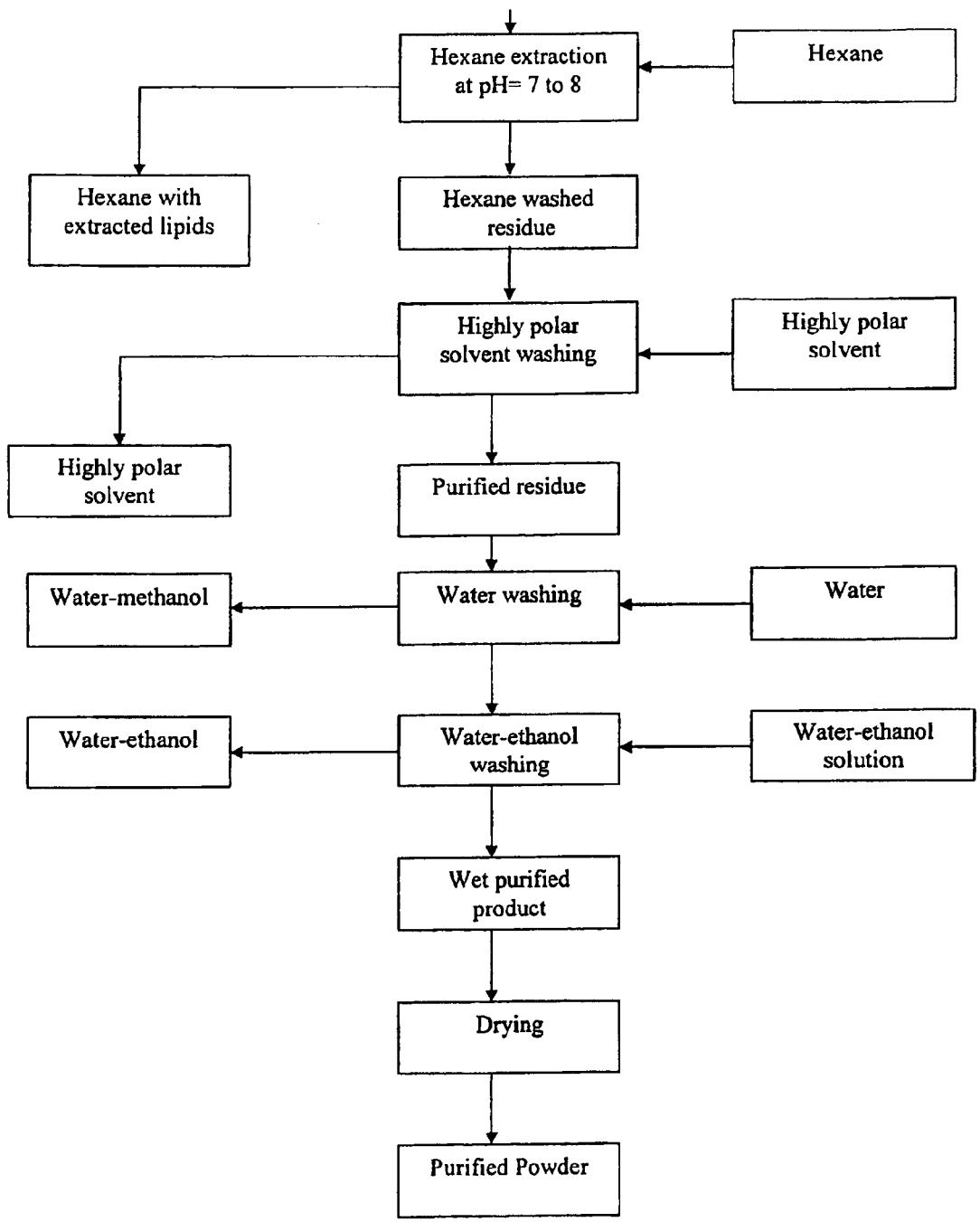

While the described embodiment represents the preferred embodiment of the present invention, it is to be understood that modifications will occur to those skilled in the art without departing from the spirit of the invention. The scope of the invention is therefore to be determined solely by the appended claims.

Embodiments of the invention are directed to a new method of purifying free xanthophylls, from plant and non-plant sources. Plant sources include marigolds (*Tagetes erecta*), LCM berries (*Lycium Chinese* Mill), boxthorn berries (*Lycium chinensis*), and green vegetables such as Kale (*Brassica oleracea* var. acephala), spinach (*Spinacia oleracea*) and Collard greens (*Brassica oleracea*, var. Champion). Other sources of raw materials include algae, silkworm excrement, and alfalfa leaves. Marigold (*Tagetes erecta*) and boxthorn berries (*Lycium chinensis*) are preferred sources.

The predominant xanthophyll extracted will depend upon the source material used. For example, many marigold specis are high in lutein. Embodiments of the invention using a marigold species high in lutein will yield predominantly lutein. If LCM berries or boxthorn berries are used, the product will be predominantly zeaxanthin. The term "predominantly" has its usual and customary meaning and, in the context of the present application, means that the particular xanthophyll species is present in excess of 50% of total carotenoids, more preferably more than 60%, yet more preferably more than 70%, yet more preferably more than 80% and most preferably more than 90% of the total carotenoids. If red peppers are used, the final product will be rich in capsanthin. Other sources may yield mixtures of xanthophylls. Naturally occurring levels of xanthophylls are known for many species and varieties. One skilled in the art would choose appropriate starting material, depending upon the desired xanthophyll product.

Embodiments of the invention are directed to a method of preparing xanthophylls. Some steps include repeated washings of the plant extract with an aqueous salt solution which facilitates the removal of water soluble impurities while lowering the pH. As the pH lowers during the salt washes, it is not necessary to add large amounts of acid to neutralize alkali used during saponification. Unlike organic solvents used in the prior art procedures, the salt water washes are environmentally friendly and do not raise health issues for end users.

Another advantage of embodiments of the method is that the purification process removes epoxides and other impurities that are released during silage and processing steps (such as drying) of the plant extracts used as the source material. As a result, the final product is virtually free of undesirable epoxide derivatives.

Embodiments of the method are commercially adaptable as solvents and other materials used in the extraction are economical and readily available.

In one preferred embodiment of the present invention, marigold extracts containing from about 40 to about 150 grams of carotenoids per kilogram and from about 5 to about 20 grams of chlorophyll per kilogram are used as starting materials. The marigold flowers used for making these extracts may be mechanically harvested or harvested by hand. Also, marigold meals or marigold extracts may be used.

Marigold meals are prepared by dehydrating the flowers. There are several ways of dehydrating, including belt, tray, shelf and drum dryers or sun drying. The dry material is milled and the process is followed by a solvent extraction using a non-polar solvent, such as for example, hexane. The solvent is then removed by evaporation and a marigold oleoresin is obtained. The oleoresin is then saponified to complete hydrolysis of the xanthophylls and chlorophylls present. Saponification may be accomplished by treatment of the oleoresin with sodium or potassium hydroxide or some other alkali. The saponification conditions are well known. Preferably, the extract is saponified without the use of any additives other than the alkali (e.g., sodium or potassium hydroxide).

Free lutein, zeaxanthin and other free xanthophylls are obtained during the saponification reaction, as well as sodium and potassium salts of fatty acids like myristic, palmitic and stearic acids. In addition, the phytyl and methyl groups on the pigment molecules may be substituted with sodium or potassium, depending on the base (e.g., NaOH or KOH, respectively) used as the saponifying agent. Water-soluble chlorophyllins may also be produced during saponification.

The saponified material is salted-out to separate the lipid pigment containing matter from the excess alkaline salts and other hydrolysis by-products with affinity or solubility in water. The salting-out treatment may be done with a common and inexpensive salt like sodium chloride or other salts which make highly polar water solutions. Such salts are well known and, in particular, include any sodium or potassium salt. The salt concentration is about 1 to 30%, preferably 5 to 15%. Repeated salt solution washings neutralize the saponified extract which avoids more expensive and difficult to use acids and/or eliminates the use of organic solvents to create aqueous and organic phases to initiate the purification process. As organic solvents have higher toxicity than aqueous salt solutions, the avoidance of an organic solvent at this step is an advantage both from the standpoint of human health and provides a cost advantage. Typically a salt solution of 5 to 15% concentration at a temperature of 85 to 90° C. is used. The pH of the salt solution is alkaline (pH 11-12). The aqueous salt washes containing the water soluble pigments are discarded leaving the oleoresin.

The oleoresin is washed with a slightly more acidic saline solution. With continued washings to work in an alkaline mixture of pH of about 6.5 to 9, and more preferably from about 7.5 to 8.0, a two phase system is formed where practically all of the water is eliminated in the aqueous-saline phase and an organic lipid phase is provided for further processing. In some embodiments, these washings may also incorporate one or more filtering steps.

This lipid phase is treated with a non-polar solvent such as hexane to form a three phase system where the upper and middle phases are decanted and eliminated thereby separating the lipids from the higher density carotenoids. The use of hexane for lipid extractions is well known in the fats and oils industry, although other straight chain hydrocarbons such as pentane, heptane, or petroleum ether (b.p. 30-60° C.) may be used.

The hexane washed material is treated with an increased polarity solvent such as alcohol mixed with water where both components are completely miscible and may contain an acidic component as part of the solution. The introduction of the increased polarity solvent reduces loss of lutein in this step of the purification. Examples of increased polarity solvents usable in this step of the invention include mixtures of alcohol/water, acetonitrile/water, acetone/water or acetic acid/water. Preferred alcohols include ethanol, methanol, propanol, isopropanol, tert-butanol, and butanol combined with water for the increased polarity solvent. Preferably, the increased polarity solvent is ethanol/water or methanol/water. More preferably, the increased polarity solvent is methanol/water. Preferably, the water content is 30% or less, more preferably 15% or less. In a most preferred embodiment, the water content is about 10%. Preferably, the increased polarity solvent includes a small amount of an acid to remove residual alkalinity, particularly in the last wash with the increased polarity solvent. Any acid may be used to acidify the increased polarity solvent including, but not limited to, HCl, $HNO_3$, $H_2SO_4$, $H_3O_4P$, at a low concentration of 1-5%, preferably 1-3%. Preferably, phosphoric acid is used at a concentration of 1-5%, preferably 2-3%. In some embodiments, the polarity of the increased polarity solvent increases through successive washes.

After washing with the increased polarity solvent, the residue is further washed with water which eliminates the excess increased polarity solvent from the system and also removes any salt or water soluble compounds.

Water is largely removed from the purified residue by mixing with a water-alcohol mixture followed by filtering under vacuum. Preferably, the alcohol is ethanol, methanol, propanol, isopropanol, tert-butanol, or butanol. Preferably, the alcohol is present at a level of at least 40%, more preferably 50%. In preferred embodiments, the water-alcohol mixture is a water-ethanol solution (50:50). This step facilities the final drying. Any residual moisture and solvent is eliminated with vacuum or freeze drying.

A preferred embodiment of the invention is described with reference to the attached FIGURE.

Marigold extract (oleoresin) free of ethoxyquin or any other additive is mixed with enough 50% aqueous solution of potassium hydroxide to saponify at 103° C. Once saponified a saline solution of sodium chloride with a concentration between 5 to 15% is added in a proportion of 4 to 8 times the weight of the starting oleoresin and at a temperature of 85 to 90° C. and stirred for about 15 minutes. The mixture is allowed to rest for 15 minutes to two hours at the same temperature until a two phase separation is formed. The bottom saline phase is drained and eliminated form the process. The remaining oleoresin is then mixed for 5 to 20 minutes with another sodium chloride solution (5 to 15%) at 85 to 90° C. rested and drained. A third saline washing may be done at 85 to 90° C. this time preferably adding 2 to 3% phosphoric acid in the solution to achieve a clearer two phase separation and better drainage of the saline phase. The residual oleoresin is then cooled to between 30 to 40° C. and washed preferably twice with a proportion of 15 parts of hexane to 1 part of residue, stirring about 10 minutes, resting for 1 to 5 hours for phase separation and decanting the upper layer. The hexane washed residue is then mixed for 5 to 15 minutes at 40 to 50° C. with an increased polarity solvent consisting of a water-methanol solution (10:90) containing between 0.5 to 1 kg of phosphoric acid per 100 liters of solution. This mixture is then vacuum filtered or centrifuged. The residual cake is then washed once to three times with a still more polar water-methanol (50:50) solution during 10 minutes at a temperature between 40 to 50° C. and vacuum filtered or centrifuged after each washing. Next the cake is washed with all the water needed at 65° C. to eliminate the residual methanol to less then 10 ppm. The water washings may be eliminated by filtration, centrifugation or decantation. The water washed residue is then washed with a water-ethanol solution (50:50) between 40 to 50° C. and vacuum filtered to eliminate the liquid. At this stage food grade antioxidants may be added to the purified residue if desired. The product is then dried to eliminate ethanol and water. Solvent elimination may be done by vacuum or freeze drying. The final product will contain between 60 to 90% free lutein and zeaxanthin where approximately 95% of these carotenoids is lutein and 5% zeaxanthin.

The typical carotenoid recovery from the starting material falls in the range of 60 to 85%.

EXAMPLES

Example 1

In a two liter reaction vessel 250 gm of marigold extract were saponified with a 50% aqueous solution of potassium hydroxide at a temperature of 103° C. The starting material contained 110.3 gm/kg of total carotenoids. The saponified material was then mixed with 1420 ml of a 9.8% sodium chloride solution in water and stirred for 20 minutes at 85° C. It was then allowed to rest for 30 minutes at 85° C. and after a two phase separation appeared, the bottom saline phase was removed with a vacuum suction. The remaining oleoresin was treated two more times with 1000 ml of a 7% sodium chloride solution as described above. The saline washed oleoresin was then transferred to a 4 L vessel and mixed vigorously with 3000 ml of hexane at 35° C. during 10 minutes. It was then allowed to rest for two and a half hours and the upper phase was decanted along with an interface containing hydrated gums. A second hexane treatment was performed in the same manner but with 1500 ml of solvent. The residual paste was then mixed with 2000 ml of a methanol-water solution (90:10) and 20 gm of 85% phosphoric acid and stirred for 10 minutes at 45° C. This dispersion was then vacuum filtered using Whatman #2 filter paper. A second methanol-water washing was done but this time with only 1000 ml of a solution with a 50:50 proportion. After this three subsequent 10 minute washings with 800 ml of water at 65° C. followed by filtration were done to eliminate the methanol. Next a 10 minute washing with 800 ml of a water-ethanol solution (50:50) was done at ambient temperature to partially eliminate water before the final drying. Drying was finished under vacuum. The purity of the end product was 84.5% total carotenoids with less than 1% volatiles representing a yield of 68.7%.

Example 2

Saponification of 100 gm of marigold extract was carried out using 36 gm of a 50% sodium hydroxide aqueous solution at a temperature of 103° C. The extract had 105 gm/kg of total carotenoids before reacting. The saponified product was stirred for 10 minutes in 500 ml of a 12% potassium chloride solution at 90° C. and rested at the same temperature for an hour. A bottom heavier phase was separated from an upper pigmented phase and this washing was repeated using the same conditions. The washed oleoresin was then mixed with 2 liters of hexane at 30° C. during 15 minutes. Mixing was then stopped and an upper hexane layer that was formed was decanted after allowing to rest for 5 hours. A thin layer of suspended solids was eliminated along with the hexane phase. A second hexane treatment was repeated with the same volume and under the same conditions and the hexane layer decanted. Excess hexane was evaporated by stirring at 55° C. and under vacuum (600 mm Hg.). The hexane washed paste was then mixed with 400 ml of an acetone-water solution (4 parts acetone to 1 part water) and 75 ml of a 25% aqueous phosphoric acid solution. The mixture was stirred for 10 minutes at 25° C. and then filtered using Whatman #2 filter paper and reduced pressure. The filter cake was washed again but this time with 100 ml of an acetone-water solution (3 parts acetone to 2 parts water) stirring 10 minutes at 25° C. and then filtered as above. The filter cake was then washed and filtered successively three times with 200 ml portions of water. The water washed paste was then mixed with 350 ml of an ethanol-water solution (1 part ethanol to 1 part water) stirring 10 minutes at 25° C. and then filtering to obtain a purified paste. The purified material was vacuum dried. A dry powder weighing 10.1 gm and having 820 gm/kg of total carotenoids determined spectrophotometrically was obtained. HPLC analysis showed that 94.7% of the carotenoids were lutein and 5.3% zeaxanthin. This product had a yield of 78.9% of total carotenoids referred to the starting material.

Example 3

A batch of 300 gm of boxthorn berries (*Lycium chinensis*) with 0.89 gm/kg of total carotenoids were soaked in 1200 ml of a 1:1 methanol:water solution for 12 hours. The berries were then homogenized in an electric blender and the total mass passed through a polyester fiber filter. The material retained in the filter was extracted with hexane at 40° C. and filtered using Whatman No. 2 filter paper. The extractions were repeated until the extract was practically colorless. This process used 5400 ml of hexane. The hexane extracts were pooled and the volume reduced to 2000 ml by evaporation under vacuum. The partially concentrated hexane extracts were then washed with 2000 ml of water to eliminate gums and other water soluble solids using separatory funnels. The water washed hexane extract was then passed through a bed of anhydrous sodium sulfate to eliminate moisture followed by solvent evaporation under vacuum to obtain a concentrated pigment extract which weighed 3 gm. The concentrate was then saponified with 2 ml of a 25% aqueous potassium hydroxide solution during 1 hour at 103° C. The saponified material was then washed three times for 20 minutes with 23.2 ml of a 7% sodium chloride solution at 65° C. separating the bottom aqueous phase after each washing. The saline washed material was then mixed with 36 ml of hexane during 10 minutes at 35° C. It was then allowed to rest for 3 hours and the upper hexane phase separated by mechanical suction. The remaining colored paste was washed with 20 ml of an 85:15 methanol:water solution at 45° C. for 10 minutes and passed through a No. 2 Whatman filter paper. The pigment on the filter was washed with 12 ml of a 50:50 methanol:water solution at 45° C. followed by three successive 9 ml water washings at 65° C., to finalize with a washing using 9 ml of a 50:50 ethanol:water solution at ambient temperature. The material was then dried under a nitrogen current. The purified material weighed 0.10 gm and after analysis showed 55% total carotenoids of which 97% was detected to be zeaxanthin and 1.1% was lutein. This represents a 20.6% yield of total carotenoids and the material was purified from 0.89 gm/kg to 550 gm/kg nearly 618 times.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A method for obtaining free xanthophylls comprising:
   providing a xanthophyll-containing plant-derived oleoresin;
   saponifying the plant-derived oleoresin to obtain a saponified resin;
   washing the saponified resin with a salt solution selected from the group consisting of a sodium or potassium salt solution;
   repeating the washing with the salt solution until the pH of the resin is about 6.5 to 9;
   washing the resin with a non-polar solvent selected from the group consisting of hexane, pentane, heptane and petroleum ether to remove lipid components;
   washing the resin at least once with an increased polarity solvent selected from the group consisting of mixtures of alcohol/water, acetonitrile/water, acetone/water, and acetic acid/water;
   washing the resin with water to remove solvent; and
   filtering and/or drying the resin to obtain free xanthophylls.

2. The method of claim 1, wherein the plant-derived oleoresin is derived from marigold (*Tagetes erecta*) or boxthorn berries (*Lycium chinensis*).

3. The method of claim 1, wherein the salt solution comprises a sodium or potassium salt at a concentration of 5 to 15%.

4. The method of claim 3, wherein the salt is a sodium salt and wherein the sodium salt is sodium chloride.

5. The method of claim 1, wherein at least one of the salt solution washes is acidified.

6. The method of claim 5, wherein the last salt solution wash is acidified.

7. The method of claim 5, wherein the at least one salt solution washes is acidified with 2-3% phosphoric acid.

8. The method of claim 1, wherein the resin is washed with the increased polarity solvent 2-4 times and wherein the polarity of the first wash is less than the polarity of the last wash.

9. The method of claim 1, wherein the increased polarity solvent is acidified.

10. The method of claim 9, wherein the resin is washed at least once with an increased polarity solvent which is acidified with 1-3% phosphoric acid.

11. The method of claim 10, wherein the increased polarity solvent comprises an acidified water:methanol (10:90) solution.

12. The method of claim 1, wherein the plant is marigold and the free xanthophylls comprise at least 60% free lutein.

13. The method of claim 1, wherein the final drying step further comprises the addition of an alcohol:water mixture to facilitate removal of water.

14. The method of claim 13, wherein the alcohol:water mixture is ethanol:water (50:50).

15. The method of claim 1, wherein the oleoresin is provided by the steps comprising:
    treating a plant homogenate with an increased polarity solvent for an initial purification;
    filtering the homogenate to obtain precipitated material; and
    extracting the precipitated material with a non-polar solvent.

16. The method of claim 15, wherein the plant is *Lycium chinensis* and the xanthophylls are predominantly zeaxanthin.

17. The method of claim 15, wherein the increased polarity solvent is a water:alcohol solution.

18. The method of claim 15, wherein the non-polar solvent is hexane.

19. The method of claim 15, further comprising:
    concentrating the extract in the non-polar solvent extracts; and
    washing the concentrate with water.

20. The method of claim 1, wherein washing the resin with the increased polarity solvent further comprises a filtering step.

* * * * *

UNITED STATES PATENT AND TRADEMARK OFFICE
CERTIFICATE OF CORRECTION

PATENT NO. : 7,629,007 B2
APPLICATION NO. : 11/640570
DATED : December 8, 2009
INVENTOR(S) : Gustavo Rodriguez Peña It is certified that error appears in the above-identified patent and that said Letters Patent is hereby corrected as shown below:

Column 3, Line 13, "free from epoxized" should be changed to --free from epoxidized--

Column 4, Line 65, "many marigold specis" should be changed to --many marigold species--

Column 9, Line 53, "or boxthom" should be changed to --or boxthorn--

Signed and Sealed this

Eleventh Day of May, 2010

David J. Kappos
*Director of the United States Patent and Trademark Office*